United States Patent
Pruckner et al.

(10) Patent No.: US 9,757,207 B2
(45) Date of Patent: Sep. 12, 2017

(54) MEDICAL OR DENTAL HANDPIECE WITH SHARED ELECTRICAL LINE

(71) Applicant: W&H Dentalwerk Bürmoos GmbH, Bürmoos (AT)

(72) Inventors: Christian Pruckner, Vienna (AT); Michael Mangelberger, St. Georgen (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 231 days.

(21) Appl. No.: 14/597,105

(22) Filed: Jan. 14, 2015

(65) Prior Publication Data

US 2015/0125809 A1     May 7, 2015

Related U.S. Application Data

(63) Continuation of application No. PCT/EP2013/065136, filed on Jul. 18, 2013.

(30) Foreign Application Priority Data

Jul. 19, 2012 (EP) .................................. 12177012

(51) Int. Cl.
    *A61C 3/00*     (2006.01)
    *A61C 1/00*     (2006.01)
    *A61C 1/08*     (2006.01)

(52) U.S. Cl.
    CPC .......... *A61C 1/0015* (2013.01); *A61C 1/0069* (2013.01); *A61C 1/088* (2013.01)

(58) Field of Classification Search
    CPC ..... A61C 1/0015; A61C 1/0069; A61C 1/088; A61N 5/062; A61N 2005/0626;
(Continued)

(56) References Cited

U.S. PATENT DOCUMENTS

| | | | |
|---|---|---|---|
| 2005/0245917 A1* | 11/2005 | Strassl | A61C 1/0046 606/17 |
| 2007/0038206 A1* | 2/2007 | Altshuler | A46B 15/0036 606/20 |
| 2007/0185553 A1* | 8/2007 | Kennedy | A61N 5/0616 607/100 |

FOREIGN PATENT DOCUMENTS

| | | |
|---|---|---|
| DE | 10259798 | 2/2004 |
| EP | 2353539 | 8/2011 |

(Continued)

OTHER PUBLICATIONS

Claims of U.S. Appl. No. 14/693,201 as of Apr. 22, 2015.*
International Search Report for PCT/EP2013/065136 (dated Sep. 5, 2013).

*Primary Examiner* — Michael Carey
(74) *Attorney, Agent, or Firm* — Klarquist Sparkman, LLP (57) ABSTRACT

A medical or dental handpiece comprises a lighting device for the emission of radiation, in particular of visible light, onto a treatment site, a temperature sensor preferably located in the interior of the handpiece, and at least one shared electrical signal line provided in the handpiece for the lighting device and the temperature sensor. The lighting device and the temperature sensor are both operatively connected to the at least one shared electrical signal line. A medical or dental treatment device comprises such a handpiece and a control and/or regulation device electrically connected to the at least one shared electrical signal line provided in the handpiece, which is designed to emit a first electrical signal assigned to the lighting device and a second electrical signal assigned to the temperature sensor.

20 Claims, 3 Drawing Sheets

(58) Field of Classification Search
CPC .... A61N 2005/0632; A61N 2005/0628; A61N 2005/0644; A61N 2005/067
USPC ....... 433/27, 29, 31; 607/88, 89, 90, 96, 102
See application file for complete search history.

(56) References Cited

FOREIGN PATENT DOCUMENTS

| | | |
|---|---|---|
| EP | 2524666 | 11/2012 |
| EP | 2524667 | 11/2012 |

* cited by examiner

MEDICAL OR DENTAL HANDPIECE WITH SHARED ELECTRICAL LINE

CROSS REFERENCE TO RELATED APPLICATION

This application is a U.S. bypass continuation application of International Application PCT/EP2013/065136, filed on Jul. 18, 2013, now completed, which in turn claims priority from European Patent Application No. 12177012.7, filed Jul. 19, 2012, now European Patent No. 2687187. The prior applications are incorporated herein by reference.

BACKGROUND

Field

This invention concerns a medical or dental handpiece with a lighting device which comprises at least one optical semiconductor element, and with a temperature measurement device.

Description of Prior Art

Patent application EP 11166638.4 discloses a medical, in particular dental, handpiece with a temperature measurement device.

SUMMARY

An object of this disclosure is to optimize the implementation or the installation arrangement of the temperature measurement device, in particular a temperature sensor, in the handpiece, preferably in the head section of the handpiece, so that despite the large number of components and the resulting sharp limitations on the space available, the temperature sensor can be located and operated in the handpiece, in particular in the head section of the handpiece.

This object is solved by means of a medical or dental handpiece, that comprises: A lighting device to emit radiation, in particular visible light, onto a treatment site, wherein the lighting device preferably has at least one optical semiconductor element, and a temperature sensor, preferably located in the interior of the handpiece and in particular capable of being supplied or operated with electrical power, wherein at least one common signal or (power) supply line for the lighting device and the temperature sensor is provided in the handpiece.

Thus in an advantageous manner a common or shared electrical signal or electrical power line is provided for the temperature sensor and the lighting device for illumination of the treatment site, via which the temperature sensor and the lighting device each receive their electrical (power supply) signals and via which the measurement signal of the temperature sensor can be conducted. This eliminates the need to provide the temperature sensor with its own electrical signal line and its own connections to a power source.

The temperature sensor that can be supplied or operated with electrical power comprises, for example, a sensor with a material whose electrical resistance is temperature-dependent, in particular an NTC resistor, an infrared sensor, or a thermocouple. The temperature sensor is in particular designed to determine the temperature of the handpiece, in particular the temperature within the interior of the handpiece, and/or the temperature of at least one component of the handpiece. The temperature sensor is preferably located on, or fastened to, a component of the handpiece, for example the outer shell, the lighting device, or a bearing. Alternatively, the temperature sensor can be located freely in an inner space in the handpiece and primarily only fastened to an electrical signal line. The temperature sensor can comprise one or more sensors.

The temperature sensor is designed to generate a temperature measurement signal, for example by means of a change to a parameter of the electrical power supply signal indicative of the temperature, for example the current amplitude.

The lighting device for the emission of radiation onto a treatment site preferably comprises one or more, for example three, four, or five, optical semiconductor elements, in particular light-emitting diodes. However, the lighting device can clearly also have other radiation sources, for example an incandescent bulb or a gas discharge lamp. The lighting device, in particular the at least one optical semiconductor element, is preferably located either on the head section of the handpiece, in particular surrounding a tool receptacle opening of the head section, or contiguous with the head section. The lighting device is in particular provided on the side of the handpiece on which the tool receptacle opening is located. The lighting device is in particular ring-shaped and preferably surrounds the tool receptacle opening of the head section. In particular, a tool may be inserted or removed through the inner hole of the ring-shaped lighting device into or out of the tool receptacle of the handpiece. Preferably at least an opening and/or a channel is provided on or in the body of the lighting device, through which a fluid, in particular a cooling medium, for example a water/air mixture, can be dispensed in the direction of the treatment site.

The common or shared electrical signal line or electrical (power) supply line provided in the handpiece, which comprises for example one or more wires, connects the lighting device and the temperature sensor to an electrical power source, in particular with a DC current source and/or a DC voltage source. The electrical power source can be located in the handpiece or provided outside the handpiece, for example in an adapter or coupling part that can be connected to the handpiece, or in a control device. The electrical power source, in particular located in the handpiece, comprises for example a battery, a rechargeable battery, or a generator, which is preferably connected to an electrical rectifier.

In accordance with one embodiment of the invention, the at least one common signal line provided in the handpiece comprises a first electrical branch line connected to the lighting device, preferably the radiation source, in particular the at least one optical semiconductor element, and a second electrical branch line connected to the temperature sensor. This makes it possible in an advantageous manner to arrange the lighting device and the temperature sensor at a spatial distance from one other, possibly far apart from one another, and each in their optimum positions.

In accordance with another embodiment, the lighting device electrically connects the at least one common electrical signal line provided in the handpiece to the temperature sensor. The lighting device preferably has a circuit board, wherein the at least one common electrical signal line provided in the handpiece is electrically connected to the temperature sensor through the circuit board or through electrical contacts located on the circuit board. This permits a particularly compact and space-saving construction, in which the lighting device, in particular its circuit board, is also designed to be the electrical conductor for the temperature sensor. The electrical contacts installed on the circuit board comprise in particular a metal alloy, preferably a metal solder (so-called metal pads).

Optionally, either 1.) the circuit board and the temperature are separated from one another and electrically connected to one another in particular through an electrical signal line, or 2.) the temperature sensor is fastened directly onto the circuit board or directly to at least one electrical contact installed on the circuit board. According to 1.), the temperature sensor can advantageously be arranged at locations and/or components and/or heat sources at a distance from the lighting device, so that in particular an erroneous measurement due to the heat generated by the lighting device can be avoided. According to 2.), a particularly compact and space-saving unit is created, consisting of the temperature sensor and the lighting device, which in particular also results in a simplification during assembly.

Preferably, the lighting device has an encapsulation with a transparent window, in particular a glass window, wherein the radiation source, preferably at least an optical semiconductor element, is held in the encapsulation and wherein preferably the encapsulation has a base which comprises the circuit board. By means of this encapsulation, the at least one optical semiconductor element is protected from contamination and negative influences. The encapsulation has in addition to the base, for example, a cap or sleeve connected to the base, on which the transparent window is located. The base and/or the cap is/are for example primarily fabricated from ceramic or glass or plastic. In accordance with a preferred embodiment, the base is primarily fabricated from ceramic or glass and the cap of metal. To connect the radiation source or the at least one optical semiconductor element to an electrical power source, the base and/or the circuit board is plated through by an electrical conductor and preferably provided with electrical contacts on an outer side, which in particular comprise a metal alloy, preferably a metal solder (so-called metal pads). In the interior of the encapsulation, in addition to the at least one optical semiconductor element there can for example be provided a conversion element for converting the wavelength of the radiation emitted by the at least one optical semiconductor element, an optical component, for example a light guide element or a reflector element, or an electrical component, for example a coil for an inductively coupled power supply to the optical semiconductor with electrical power, or an element for adaptation of the electrical voltage and/or electrical current for the at least one semiconductor element.

The temperature sensor is preferably fastened directly or indirectly (mechanically) to the lighting device, so that the temperature sensor and the lighting device preferably form a unit, in particular a unit that is inseparably connected together. A direct mechanical fastening can be obtained, for example, by soldering the temperature sensor to the circuit board or to an electrical contact installed on it, in particular a metal alloy. An indirect mechanical fastening can be achieved, for example, by means of an electrical signal line which connects the circuit board or an electrical contact installed on it, in particular a metal alloy, to the temperature sensor and is fastened to it. A mechanical fastening of the temperature sensor to the lighting device simplifies, for example, the assembly and positioning of the temperature sensor in the handpiece.

In accordance with one embodiment, the handpiece comprises a head part, on which a tool receptacle or tool holding device that can be set in motion is provided, wherein the temperature sensor is located in the head part or contiguous with the head part. The temperature sensor is preferably in the immediate vicinity of one or more (potential) heat sources, preferably in the immediate vicinity of one or more (potential) heat sources located in the head part, in particular of components of the handpiece that can be set in motion, such as for example the tool holding device, bearings for the tool holding device, etc. Preferably, the lighting device for the emission of radiation, in particular of visible light, in particular the radiation source, preferably the at least one optical semiconductor element, is located on the handpiece in such a way that the radiation emitted can be directed directly towards or onto the treatment site. Particularly preferably, the lighting device, in particular the at least one optical semiconductor element, is also located in the head part, on the head part, or contiguous with the head part. Thus the shared supply of the temperature sensor and the lighting device with electrical signals is possible in an advantageous manner through at least a majority of the length of the handpiece.

The lighting device and the temperature sensor can be electrically connected in parallel or in series. The lighting device and the temperature sensor are or can be connected through the shared electrical signal line provided in the handpiece to a single, shared power source.

A medical, in particular dental, treatment device, comprises a handpiece with a lighting device for the emission of radiation, in particular of visible light, onto a treatment site, wherein the lighting device preferably has at least one optical semiconductor element, a temperature sensor preferably located in the interior of the handpiece, and at least one common or shared electrical signal line provided in the handpiece for the lighting device and the temperature sensor and a control and/or regulation device electrically connected to the at least one common or shared electrical signal line provided in the handpiece, said control and/or regulation device is designed to emit, on an alternating or time-offset basis, a first electrical (power supply) signal associated with the lighting device, in particular with the at least one optical semiconductor element, and a second electrical (power supply) signal associated with the temperature sensor. The control and/or regulation device preferably comprises a microcontroller. The first and the second electrical signal preferably differ from one another in at least one parameter, for example in the direction of current flow, in the value of the electrical voltage or the electrical current. As a result, the control and/or regulation device is designed to send the first and second electrical signals in different directions of current flow (by means of a change in the direction of electrical potentials) and/or to generate a first and a second electrical signal with different values of electrical voltages and/or electrical currents. The control and/or regulation device preferably has a constant current source to generate the first electrical signal and a constant voltage source to generate the second electrical signal. These measures make it possible in an advantageous manner to ensure that the lighting device or the temperature sensor receive a matching (first or second) electrical power supply signal.

In accordance with one embodiment, the control and/or regulation device is designed to receive a temperature measurement signal from the temperature sensor, to compare said temperature measurement signal with a predetermined temperature limit value, and to interrupt the operation of the handpiece should the predetermined temperature limit value be reached or exceeded, or to change, in particular to reduce, the power of a drive of the handpiece and/or to actuate a warning device to warn the user. To interrupt operation or to change the power of the handpiece, the control and/or regulation device is for example designed to cease or to change the emission or conduction of a drive signal and/or of a drive medium to a drive, for example to an electrically or air-driven motor or to a fluid-driven turbine. The warning device may for example be implemented by means of an acoustic signal emission device, a visual display unit, for example at least a light-emitting diode on the handpiece or a display, or by means of a tactile signal emission device. The warning device is for example connected electrically to the control and/or regulation device or is designed as a part of the control and/or regulation device.

A method for operating such a medical, in particular dental, treatment device is defined in that the control and/or regulation device alternately emits a first electrical signal to the lighting device, in particular to the at least one optical semiconductor element, and a second electrical signal to the temperature sensor. The control and/or regulation device preferably alternately generates, by changing the direction of the electrical potential and the direction of current flow, a first electrical signal using a constant current source and a second electrical signal using a constant voltage source, so that the first and second electrical signal flow in different directions of current flow.

In accordance with an alternative embodiment, it is also possible to design a method for the operation of such a medical, in particular dental, treatment device in which the first electrical (power supply) signal associated with the lighting device, in particular the at least one optical semiconductor element, and the second electrical (power supply) signal associated with the temperature sensor, can be or are primarily emitted simultaneous by a control and/or regulation device. The first and second signals are thereby preferably formed by a constant current with an alternating component modulated thereon, or an alternating current portion modulated thereon. It is therefore possible to supply the lighting device and the temperature sensor with power simultaneously.

A corresponding medical, in particular dental, treatment device, comprises a handpiece with a lighting device for the emission of radiation, in particular of visible light, onto a treatment site, wherein the lighting device preferably has at least one optical semiconductor element, a temperature sensor preferably located in the interior of the handpiece, and at least one common or shared electrical signal line provided in the handpiece for the lighting device and the temperature sensor and a control and/or regulation device electrically connected to the at least one common or shared electrical signal line provided in the handpiece, said control and/or regulation device is designed to emit, simultaneously, a first electrical (power supply) signal associated with the lighting device, in particular with the at least one optical semiconductor element, and a second electrical (power supply) signal associated with the temperature sensor. The first and second signals are thereby preferably formed by an electrical power supply signal comprising a constant current with an alternating component modulated thereon, or an alternating current portion modulated thereon. The lighting device, preferably the at least one optical semiconductor element, and the temperature sensor are in particular electrically connected in parallel or in series. The temperature sensor is connected in series with an upstream filter or an electrical gate to filter the direct current and alternating current portions of the electrical power supply signal, for example a condenser.

The treatment device comprises for example a constant current source for the emission of a constant current, in particular for the supply of power to the lighting device or to the at least one optical semiconductor element, as well as an electrical device designed to modulate an alternating component/portion or alternating current portion onto the constant current. The modulated alternating (current) portion is provided for the supply to the temperature sensor and may be for example about 5%-15%, preferably about 10%, of the current rating of the constant current, for example about 4 mA. The temperature sensor, which in particular comprises a material with an electrical resistance that is temperature-dependent, preferably an NTC resistor, is designed to change depending on the temperature the voltage value of the electrical power supply signal, in particular of the modulated alternating (current) portion, whereby a temperature measurement signal is formed. The control and/or regulation device is designed, as described above, to receive the voltage value or the temperature measurement signal, to compare it with a comparison value, and to stop or change the operation of the handpiece, and/or to generate a warning signal.

The invention will now be explained below on the basis of preferred embodiments and making reference to the accompanying drawings:

DETAILED DESCRIPTION

The units shown in FIGS. 1A-5B for temperature measurement and lighting, in particularly having a shared electrical supply, have a similar or identical design in many features, so that the following description applies to all these units in FIGS. 1A-5B. Similar or identical components are provided with the same numerals.

Figure 7:
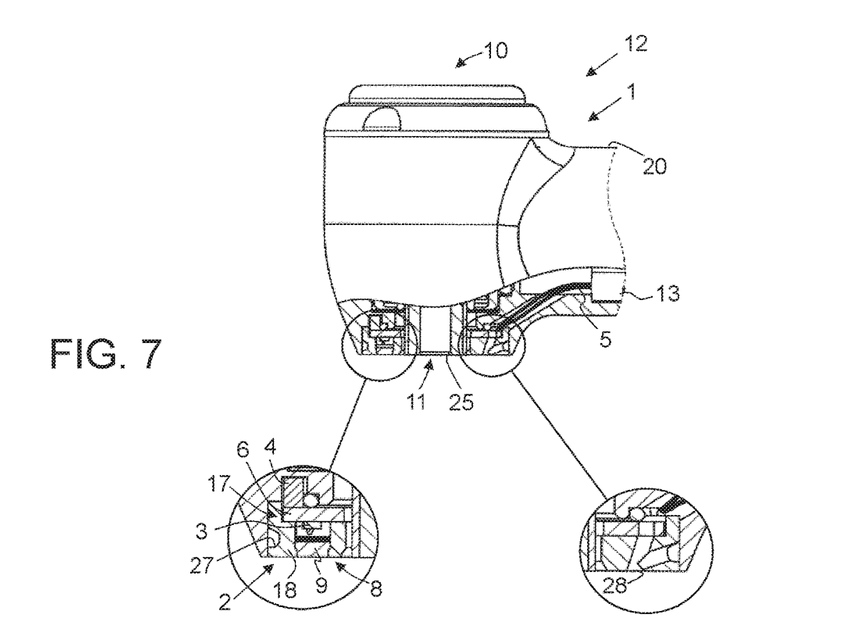
FIGS. 7 and 8 display two different embodiments of medical or dental treatment devices or medical, in particular dental, handpieces each with a unit that comprises a lighting device with an optical semiconductor element for the emission of radiation, a temperature sensor, and a shared or common electrical signal line for the optical semiconductor element and the temperature sensor.
Figure 8:
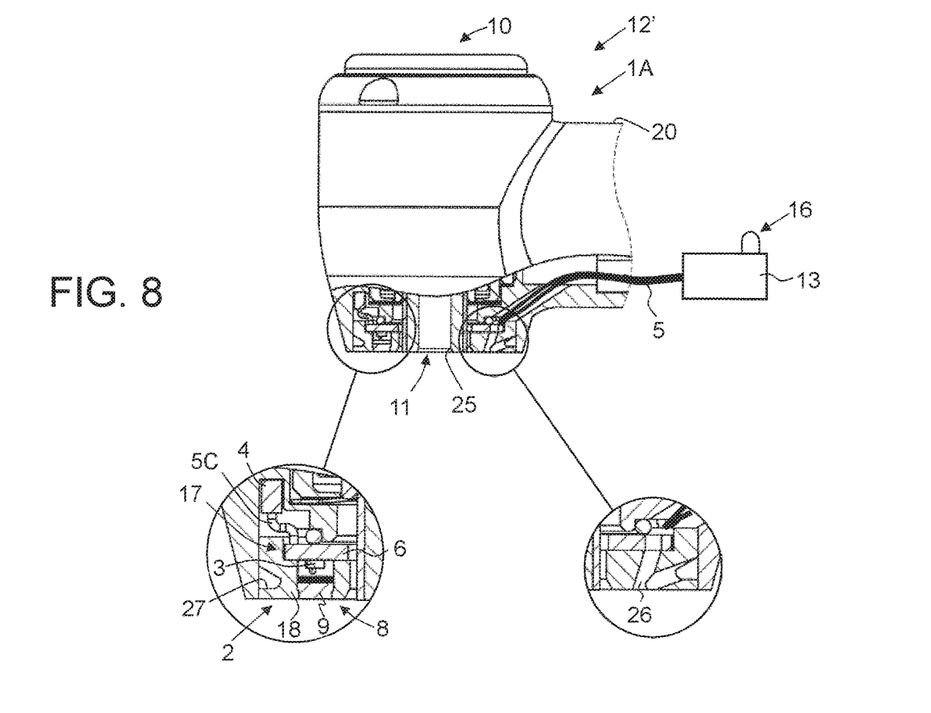

The units for temperature measurement and lighting comprise a temperature sensor 4, a lighting device 2, and a shared or common electrical signal line or (power) supply line 5. As can be seen in FIGS. 7 and 8, the shared electrical signal line 5 is provided in the interior of a handpiece 1, 1A, in particular in the interior of an outer shell 20 of the handpiece 1, 1A.

The temperature sensor 4 comprises an electrical or electrically powered sensor, for example a sensor with a material whose electrical resistance is temperature-dependent, in particular an NTC resistor, an infrared sensor, or a thermocouple. The temperature sensor 4 is in particular designed to determine the temperature of a handpiece 1, 1A (see FIGS. 7 and 8), in particular the temperature within the interior of the handpiece 1, 1A, and/or the temperature of at least one component of the handpiece 1, 1A.

The lighting device 2 comprises at least one optical semiconductor element 3. The at least one optical semiconductor element 3 is fastened onto a circuit board 6. The circuit board 6 preferably comprises electrically nonconducting material, such as ceramic material or glass-ceramic material or glass or plastic. The circuit board 6 mechanically and in particular electrically connects the at least one optical semiconductor element 3 to the electrical signal line 5. To this end, the circuit board 6 is penetrated by electrical conductors that are preferably held in holes of the circuit board 6 and that connect the semiconductor element 3 to the electrical signal line 5, and/or the circuit board 6 comprises electrically conductive layers and/or contacts 7A, 7B, 7C located on at least one of its surfaces. The circuit board 6 is part of a base 17 of the lighting device 2 or preferably forms the base 17.

The lighting device 2 furthermore comprises a shell 18 and a transparent window 9. The shell 18 is for example made of metal or an electrically nonconductive material such as for example ceramic material or glass or plastic. The transparent window 9 is designed and located in such a way that radiation emitted by the at least one optical semiconductor element 3 can be emitted through window 9 into the environment. The window 9 comprises for example an oxide glass or a silicate glass or a chalcogenide glass. The window 9 is preferably designed as an optical element or comprises such an optical element, for example a lens or a beam guide.

The shell 18 has a hole or a through hole. The transparent window 9 and the circuit board 6 or base 17 seal the through hole of the hollow shell 18 in such a way that a preferably hermetically sealed chamber 19 is formed in which the at least one optical semiconductor element 3 is received. The circuit board 6 and/or the base 17, the shell 18, and the window 9 thus form an encapsulation 8 surrounding or enclosing the at least one optical semiconductor element 3. In the interior of the chamber 19 or encapsulation 8, in addition to the at least one optical semiconductor element 3, there can be provided a conversion element 21 for converting the wavelength of the radiation emitted by the at least one optical semiconductor element 3, an optical component, for example a light guide element or a reflector element, or an electrical component for adaptation or transmission of the electrical voltage and/or electrical current for the at least one semiconductor element 3.

The encapsulation 8 preferably comprises a base 17 made of ceramic material and a metallic shell 18, which are connected and/or soldered together by means of a material containing metal and glass and/or a metal alloy, in particular a metal solder, and/or a casting or adhesive material, for example a silicone or epoxy resin or a silicone or epoxy adhesive. The material containing metal and glass in particular comprises a mixture of metal and glass particles. Particularly preferably, at least one electrical contact, for example an electrical contact 7A, 7B, 7C on the surface of the base 17 and/or an electrical contact penetrating the base, which is/are designed to connect the optical semiconductor element 3 to the electrical signal line 5 or to an electrical power source, comprises a material containing metal and glass, in particular a mixture of metal and glass particles. The electrical contacts 7A, 7B, 7C are electrically separated or insulated from one another, in particular by spacing them apart from one another on the circuit board 6 having an electrically insulating material, or arranging them on a base 17 having an electrically insulating material.

Figure 6:
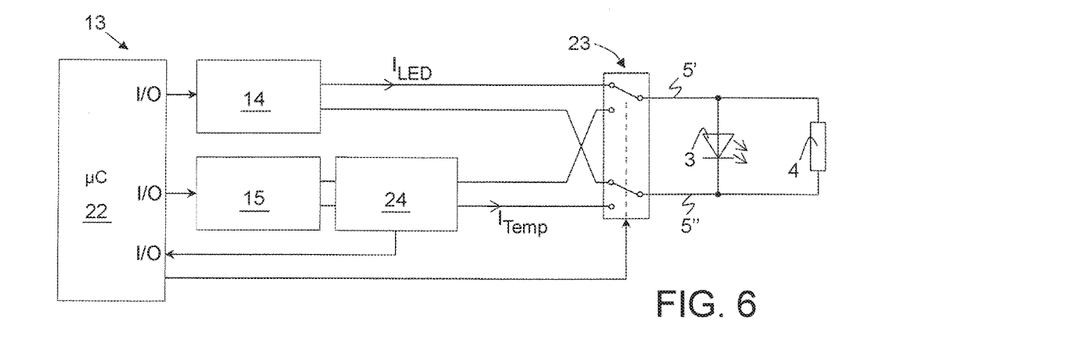
FIG. 6 shows a schematic representation of a control and/or regulation device that alternately emits a first electrical signal associated with the lighting device and a second electrical signal associated with the temperature sensor.

The shared or common electrical signal line 5 connects the lighting device 2, in particular the at least one optical semiconductor element 3, and the temperature sensor 4 to one or more electrical power sources 14, 15 (see FIG. 6). The shared electrical signal line 5 is furthermore designed to transmit a measurement signal from the temperature sensor 4 to a control and/or regulation device 13 (see FIG. 6). As a result, the shared electrical signal line 5 is or can be electrically connected to the control and/or regulation device 13. The shared electrical signal line 5 comprises at least an electrically conducting, preferably electrically insulated, conductor or wire, for example a copper wire.

Figure 1A:
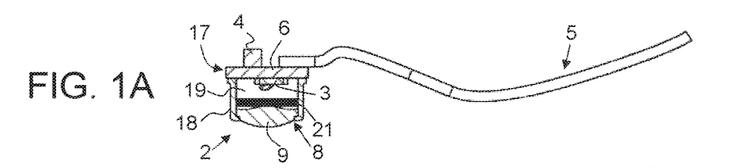
FIGS. 1A and 1B, 2A and 2B, 3A and 3B, 4A and 4B, and 5A and 5B show a cutaway side view and a top view of five different embodiments of a unit, respectively, that comprises a lighting device with an optical semiconductor element for the emission of radiation, a temperature sensor, and a shared or common electrical signal line for the optical semiconductor element and the temperature sensor.
Figure 1B:
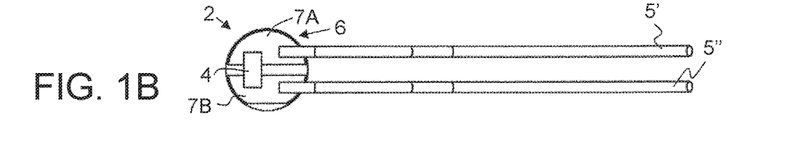

In the following, the different features of the embodiments in FIGS. 1A, 1B; 2A, 2B; 3A, 3B; 4A, 4B; 5A, 5B are described:

In the embodiments shown in FIGS. 1A, 1B; 2A, 2B; 3A, 3B, the lighting device 2, in particular the base 17 or the circuit board 6, connects temperature sensor 4 electrically to the at least one shared electrical signal line 5. To this end, there are provided on the base 17 or on the circuit board 6, in particular on a surface of base 17 or circuit board 6, electrically conductive contacts 7A, 7B, 7C, in particular metal alloys (so-called metal pads) that are electrically connected, for example soldered, to the shared electrical signal line 5. From these electrical contacts 7A, 7B, 7C there is formed an electrical connection (already described above) through or via base 17 or circuit board 6 to the at least one optical semiconductor element 3, so that the optical semiconductor element 3 can be supplied with electrical power. Furthermore the electrical contacts 7A, 7B, 7C electrically connect the shared electrical signal line 5 to temperature sensor 4, so that temperature sensor 4 can be supplied with electrical power and a measurement signal from temperature sensor 4 can be transmitted through the shared electrical signal line 5 to a control and/or regulation device 13.

In the embodiments in FIGS. 1A, 1B; 2A, 2B, the temperature sensor 4 is fastened directly to the circuit board 6/the base 17 or directly to at least one electrical contact 7A, 7B, 7C mounted on the circuit board 6/the base 17. Accordingly, temperature sensor 4 is preferably designed as a surface-mounted component (SMD component) and is in particular fastened, for example soldered, to at least one electrical contact 7A, 7B, 7C by surface mounting.

In the embodiment shown in FIGS. 1A, 1B, the temperature sensor 4, for example a sensor with a material whose electrical resistance is temperature-dependent, in particular an NTC resistor, and the at least one optical semiconductor element 3 are arranged or connected electrically in parallel. To achieve this, two contacts 7A, 7B are provided on circuit board 6/base 17 and electrically insulated from one another, wherein each electrical contact or connection of the temperature sensor 4 is connected with one of the electrical contacts 7A, 7B. In the same way, each electrical contact or connection of the at least one optical semiconductor element 3 is connected with one of the electrical contacts 7A, 7B. Furthermore, each of the two electrical contacts 7A, 7B is electrically connected to one of the conductors 5', 5" of the shared electrical signal line 5. Electrical power is thus supplied for the optical semiconductor element 3 for example from conductor 5' through contact 7A, the optical semiconductor element 3 and contact 7B into conductor 5". Electrical power is supplied for the temperature sensor 4 for example from conductor 5" via contact 7B, the temperature sensor 4 and contact 7A into conductor 5'. The shared electrical signal line 5, for example conductor 5' thereof, is thus also designed to transmit the temperature measurement signal to the control and/or regulation device 13. The current flow directions described are examples and it is therefore clearly also possible that the current flow directions for temperature sensor 4 and the optical semiconductor element 3 are arranged in the opposite manner.

Figure 3A:
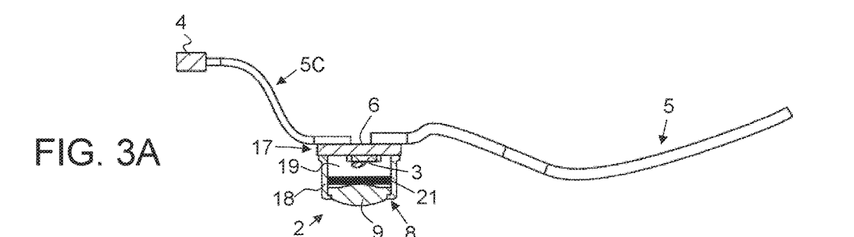
Figure 3B:
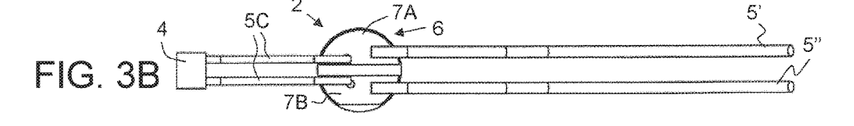
Figure 4A:
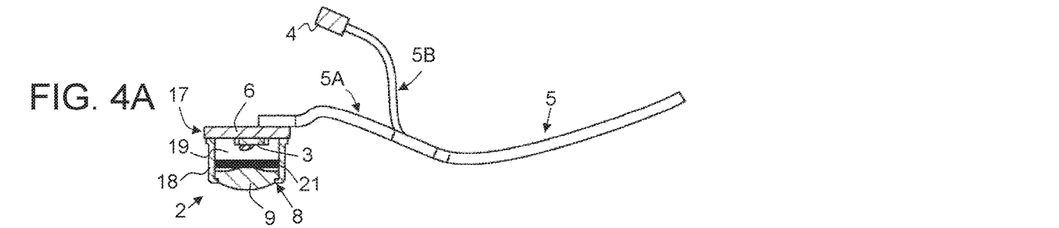
Figure 4B:
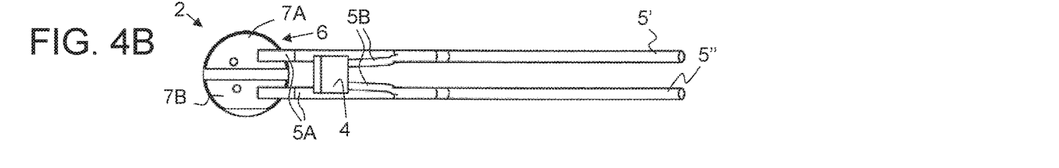

The supply of the optical semiconductor element 3 and temperature sensor 4 with electrical power as well as the signal transmission of the electrical temperature measured value in the embodiment shown in FIGS. 1A, 1B and in all other embodiments in which temperature sensor 4 and the at least one optical semiconductor element 3 are arranged or connected electrically in parallel (FIG. 3A, 3B; FIG. 4A, 4B), preferably takes place with a time offset or alternately and/or by means of switching between a constant current source and a constant voltage source and/or by changing the direction of electrical potentials and therefore the current flow direction in supplying the optical semiconductor element 3 with a first electrical signal and supplying the temperature sensor 4 with a second electrical signal. This will be further described in detail with reference to FIG. 6.

Figure 2A:
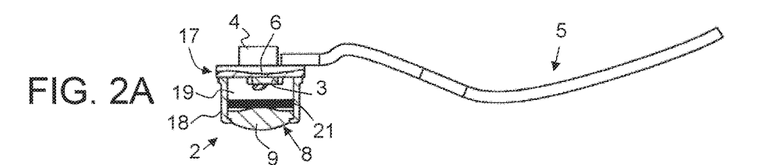
Figure 2B:
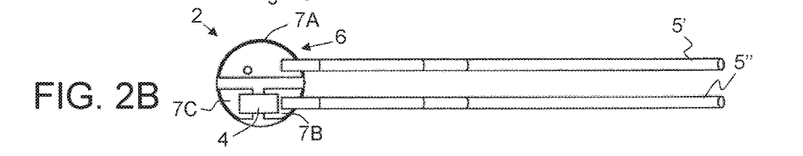

In the embodiment shown in FIGS. 2A, 2B, the temperature sensor 4, for example a sensor with a material whose electrical resistance is temperature-dependent, in particular an NTC resistor, and the at least one optical semiconductor element 3 are arranged or connected electrically in series. On circuit board 6/base 17 there are three contacts 7A, 7B, 7C provided, insulated electrically from one another, wherein two electrical contacts 7A, 7B are each electrically connected to one conductor 5', 5" of the shared electrical signal line 5. The temperature sensor 4 is connected by each of its electrical contacts or connections to one of the electrical contacts 7B and 7C. Finally, each electrical contact or connection of the at least one optical semiconductor element 3 is connected with one of the electrical contacts 7A, 7C. Accordingly, the supply of electrical power for the temperature sensor 4 and for the optical semiconductor element 3 and the transmission of measurement signals takes place simultaneously, for example from conductor 5' through contact 7A, the optical semiconductor element 3, the electrical contact 7C, the temperature sensor 4 and the contact 7B, into the conductor 5' (or alternatively in the opposite current flow direction).

To supply the temperature sensor 4 and the optical semiconductor element 3 with electrical power and to determine the temperature measured value in accordance with the embodiment shown in FIGS. 2A, 2B and all other embodiments in which the temperature sensor 4 and the at least one optical semiconductor element 3 are arranged or connected electrically in series (FIG. 5A, 5B), a control and/or regulation device is provided with, for example, a constant voltage source that is designed to electrically supply a constant current source which provides a constant current to the lighting device 2, in particular the at least one semiconductor element 3. Furthermore, a current regulator is provided that is designed to compensate for the temperature-dependent voltage changes caused by temperature sensor 4. A monitoring unit connected to the current regulator is designed to detect the regulating behavior of the current regulator and to determine a temperature measured value based on the regulating behavior detected.

In the embodiment shown in FIGS. 3A, 3B, the circuit board 6 or base 17 and the temperature sensor 4 are separate from one another and electrically connected to one another through an electrical signal line 5C. The electrical signal line 5C is electrically connected to the electrical contacts 7A, 7B, in particular also mechanically fastened to it, for example, soldered to it. Otherwise, the structure and function of the electrical signal line 5C correspond to the structure and function of the shared electrical signal line 5 described above. Electrical power is thus supplied for the optical semiconductor element 3 for example from conductor 5' through contact 7A, the optical semiconductor element 3 and contact 7B into conductor 5". Electrical power is supplied for the temperature sensor 4 for example from conductor 5" through contact 7B, a first electrical conductor of signal line 5C, the temperature sensor 4, a second electrical conductor of signal line 5C, and the contact 7A into the conductor 5'. Conductor 5' is thus also designed to transmit the temperature measurement signal to the control and/or regulation device 13. The current flow directions described are examples and it is therefore clearly also possible for the current flow directions for temperature sensor 4 and the optical semiconductor element 3 to be reversed.

The temperature sensor 4, for example a sensor with a material whose electrical resistance is temperature-dependent, in particular an NTC resistor, and the at least one optical semiconductor element 3 are again arranged or connected electrically in parallel. The supply of the optical semiconductor element 3 and the temperature sensor 4 with electrical power and the signal transmission of the temperature measured value accordingly takes place in the same manner as described for the embodiment in FIGS. 1A, 1B and is described in further detail with reference to FIG. 6.

Of course, it is also possible for circuit board 6 or base 17 and temperature sensor 4 to be separate from one another and to be arranged electrically connected to one another via an electrical signal line 5C, and to be arranged or connected electrically in series. Such an embodiment comprises for example a circuit board 6 or a base 17 with three electrical contacts 7A, 7B, 7C, as shown in FIG. 2B, as well as a temperature sensor 4 that is electrically connected to two contacts 7B, 7C via a signal line 5C as shown in FIGS. 3A, 3B.

In the embodiment shown in FIGS. 4A, 4B, the at least one common or shared electrical signal line 5 has a first electrical branch line 5A connected to the at least one optical semiconductor element 3, and a second electrical branch line 5B connected to the temperature sensor 4. The branch lines 5A, 5B are for example soldered or mechanically connected to the electrical signal line 5 and/or to one another. The embodiment according to FIGS. 4A, 4B shows the temperature sensor 4, for example a thermocouple, and the optical semiconductor element 3 arranged electrically in parallel with one another, so that the supply of the optical semiconductor element 3 and the temperature sensor 4 with electrical power takes place in accordance with the embodiment in FIGS. 1A, 1B and/or FIG. 6.

Figure 5A:
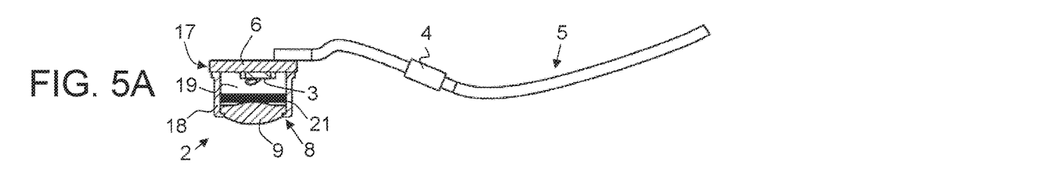
Figure 5B:
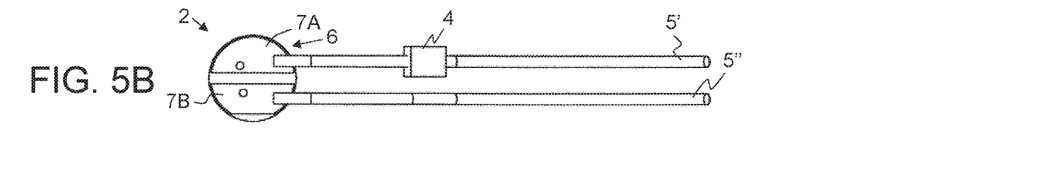

The embodiment according to FIGS. 5A, 5B shows the temperature sensor 4, for example a thermocouple, and the optical semiconductor element 3 arranged electrically in series with one another. The temperature sensor 4 is in particular directly integrated into electrical signal line 5 or at least into one of its conductors 5', 5". The electrical power supply of the temperature sensor 4 and the optical semiconductor element 3 as well as determination of the temperature measured value takes place exactly as described above for FIGS. 2A, 2B.

FIG. 6 shows a schematic diagram of a control and/or regulation device 13, preferably with a microcontroller 22, with an electrical power source in the form of a direct current and/or direct voltage source, and with a switching device 23. The control and/or regulation device 13 is provided for the supply of temperature sensor 4 and the at least one optical semiconductor element 3 with electrical power, in particular when temperature sensor 4 and the semiconductor element are arranged or connected electrically in parallel (see for example FIG. 1A, 1B; 3A, 3B, FIG. 4A, 4B).

The electrical power source comprises a constant current source 14 and a constant voltage source 15. The control and/or regulation device 13 or the switching device 23 are designed to connect the at least one optical semiconductor element 3 of lighting device 2 and the temperature sensor 4 to the electrical power source in a time-offset or alternating manner via the shared electrical signal line 5, 5', 5''. The control and/or regulation device 13 or switching device 23 are in particular designed to use switching between the constant current source 14 and the constant voltage source 15 to alternately provide the at least one optical semiconductor element 3 with a first electrical signal in the form of a constant current ($I_{LED}$) and the temperature sensor 4 with a second electrical signal in the form of an electric current ($I_{TEMP}$). The control and/or regulation device 13 is finally designed to change the direction of the electrical potentials and therefore the direction of current flow to the optical semiconductor element 3 and the temperature sensor 4 to provide the electrical power in different or opposing directions of current flow, so that in particular the second electrical signal ($I_{TEMP}$) assigned to the temperature sensor 4 flows in the blocking direction of the optical semiconductor element 3 and therefore does not flow through the optical semiconductor element 3. The frequency at which the first and second electrical signals are emitted alternately lies roughly in a range greater than 25 Hz, preferably at around 50-100 Hz.

The control and/or regulation device 13 furthermore comprises a compensation device or compensation network 24 which is designed to adjust the second electrical signal ($I_{TEMP}$) or temperature measurement signal (after passing temperature sensor 4), in particular its voltage, in such a way that the microcontroller 22 can process or evaluate the signal. The compensation device 24 and/or the microcontroller 22 can have additional devices for processing the second electrical signal ($I_{TEMP}$) or temperature measurement signal, for example a filter, a signal amplifier, or an analog-to-digital converter.

The control and/or regulation device 13 is designed to receive a temperature measurement signal from the temperature sensor 4, compare it with a predetermined temperature limit value, and, should the predetermined limit value be reached or exceeded, to interrupt the operation of the handpiece 1, 1A and/or to actuate a warning device 16 (see FIG. 8) to warn the user.

FIGS. 7 and 8 show two medical or dental treatment devices 12, 12', which comprise: A medical, in particular dental, handpiece 1, 1A, a temperature sensor 4, a lighting device 2, a control and/or regulation device 13, which is in particular designed to alternately emit a first electrical signal assigned to the lighting device 2, in particular to the at least one optical semiconductor element 3, and a second electrical signal assigned to the temperature sensor 4, and at least one shared electrical signal line 5 provided in the handpiece 1, 1A, that electrically connects the temperature sensor 4 and the lighting device 2 to an electrical power source.

The handpieces 1, 1A have a head part 10 on which a tool holder 11 that can be set into a working motion and a tool receptacle opening 25 are provided. Preferably, the temperature sensor 4 and lighting device 2 are also provided on or in the head part 10. Other components can also be provided on or in head part 10, for example a tool-releasing device for the release of a tool from the tool holder 11, a drive element, for example a gear or a turbine that can be driven by compressed gas, or at least a bearing for the movable support of the tool holder 11, for example a roller bearing.

The lighting device 2 is designed annularly around the tool receptacle opening 25 and comprises a body and a through-bore penetrating the body, via said through-bore a tool can be inserted into the tool receptacle opening 25 and the tool holder 11. Preferably there is at least one bore 26 and/or at least one ring channel 27 and/or at least one opening 28 provided on and/or in the body of the lighting device 2, which is/are connected, for example via a fluid line, to a fluid source, for example a water and/or compressed air source. The lighting device 2 furthermore electrically connects the at least one shared or common electrical signal line 5 provided in handpiece 1, 1A to the temperature sensor 4. The lighting device 2 and temperature sensor 4 are electrically arranged in parallel with one another.

The temperature sensor 4 shown in FIG. 7, for example a sensor with a material whose electrical resistance is temperature-dependent, in particular an NTC resistor, is fastened directly onto circuit board 6/the base 17 or directly to at least one electrical contact 7A, 7B, 7C of the lighting device 2 mounted on the circuit board 6/the base 17. The arrangement of temperature sensor 4 in particular corresponds to the embodiment according to FIGS. 1A, 1B, so that the features described in connection with FIGS. 1A, 1B also apply to the temperature sensor 4, the lighting device 2, and the one shared electrical signal line 5 in FIG. 7.

In contrast, the temperature sensor 4 in FIG. 8, for example a sensor with a material whose electrical resistance is temperature-dependent, in particular an NTC resistor, is offset from the circuit board 6 or the base 17 and electrically connected to the circuit board 6 or the base 17 through an electrical signal line 5C. The arrangement of the temperature sensor 4 in particular corresponds to the embodiment according to FIGS. 3A, 3B, so that the features described in connection with FIGS. 3A, 3B also apply to the temperature sensor 4, the lighting device 2, and the one shared electrical signal line 5 in FIG. 8.

The control and/or regulation device 13 shown in FIGS. 7 and 8 corresponds in particular in terms of their structure and/or their function to the control and/or regulation device 13 in FIG. 6, so that the features described in connection with FIG. 6 also apply to the control and/or regulation devices 13 in FIGS. 7 and 8. The control and/or regulation device 13 is either provided in the handpiece 1 (see FIG. 7) or outside the handpiece 1A (see FIG. 8), for example in a supply unit that is connected to handpiece 1A through a supply line. A warning device 16 to warn the user of the reaching or exceeding of a temperature value is either provided directly on the control and/or regulation device 13 (see FIG. 8) or electrically connected to it via a line.

The invention is not limited to the embodiments described here, but instead comprises all embodiments deploying or including the basic, analogous functional principle of the invention. In addition, all the features of all the embodiments described and illustrated here may be combined with one another.

What is claimed is:
1. A medical or dental handpiece comprising:
   a lighting device for the emission of radiation onto a treatment site,
   a temperature sensor, and
   at least one shared electrical line provided in the handpiece and coupled to the lighting device and the temperature sensor, wherein power for the lighting device and at least one of power for the temperature sensor or a temperature measurement signal of the temperature sensor are transmitted on the shared electrical line alternately or with a time offset.
2. The medical or dental handpiece according to claim 1, wherein the at least one shared electrical line provided in the handpiece comprises a first electrical branch line connected to the lighting device and a second electrical branch line connected to the temperature sensor.

3. The medical or dental handpiece according to claim 1, wherein the lighting device electrically connects the at least one shared electrical line provided in the handpiece to the temperature sensor.

4. The medical or dental handpiece according to claim 3, wherein the lighting device comprises a circuit board, wherein the at least one shared electrical line provided in the handpiece is electrically connected through the circuit board or through electrical contacts mounted on the circuit board to the temperature sensor.

5. The medical or dental handpiece according to claim 4, wherein the circuit board and the temperature sensor are physically separated from one another and electrically connected to one another through an electrical line.

6. The medical or dental handpiece according to claim 4, wherein the temperature sensor is fastened directly onto the circuit board or directly onto at least one electrical contact mounted on the circuit board.

7. The medical or dental handpiece according to claim 1, wherein the lighting device comprises an encapsulation with a transparent window, wherein at least one optical semiconductor element is held in the encapsulation and wherein the encapsulation has a base comprising a circuit board.

8. The medical or dental handpiece according claim 1, wherein the temperature sensor is fastened directly or indirectly to the lighting device.

9. The medical or dental handpiece according claim 1, wherein the handpiece comprises a head part on which a tool holder is provided that can be set in motion by a drive element, wherein the temperature sensor is disposed in the head part or contiguous with the head part.

10. A medical or dental treatment device comprising:
a medical or dental handpiece comprising
a lighting device for the emission of radiation onto a treatment site,
a temperature sensor, and
at least one shared electrical wire provided in the handpiece and coupled to the lighting device and the temperature sensor, wherein power for the lighting device and a temperature measurement signal of the temperature sensor are each transmitted on the at least one shared electrical wire, and
a control and/or regulation device electrically connected to the at least one shared electrical wire and designed to emit a first electrical signal assigned to the lighting device for power supply and a second electrical signal assigned to the temperature sensor.

11. The medical or dental treatment device according to claim 10, wherein the control and/or regulation device is designed to emit the first electrical signal and the second electrical signal alternately or with a time offset.

12. The medical or dental treatment device according to claim 10, wherein the control and/or regulation device is designed to transmit the first and second electrical signals in different current flow directions.

13. The medical or dental treatment device according to claim 10, wherein the control and/or regulation device comprises a constant current source to generate the first electrical signal and a constant voltage source to generate the second electrical signal.

14. The medical or dental treatment device according to claim 10, wherein the control and/or regulation device is designed to emit the first electrical signal and the second electrical signal substantially simultaneously.

15. The medical or dental treatment device according to claim 14, wherein the first and second electrical signals are formed by a constant current with an alternating component or an alternating current portion modulated thereon.

16. The medical or dental treatment device according to claim 10, wherein the control and/or regulation device is designed to receive the temperature measurement signal from the temperature sensor, to compare the temperature measurement signal with a predetermined temperature limit value, and to interrupt the operation of the handpiece, or to change a power of a drive of the handpiece and/or to actuate a warning device to warn the user, when the predetermined temperature limit value is reached or exceeded.

17. The medical or dental treatment device according to claim 10, wherein the lighting device electrically connects the at least one shared electrical wire provided in the handpiece to the temperature sensor.

18. The medical or dental treatment device according to claim 17, wherein the lighting device comprises a circuit board, wherein the at least one shared electrical wire provided in the handpiece is electrically connected through the circuit board or through electrical contacts mounted on the circuit board to the temperature sensor.

19. The medical or dental treatment device according to claim 18, wherein the temperature sensor is fastened directly onto the circuit board or directly onto at least one electrical contact mounted on the circuit board.

20. A medical or dental handpiece comprising:
a lighting device for the emission of radiation onto a treatment site,
a temperature sensor, and
at least one shared electrical line provided in the handpiece and coupled to the lighting device and the temperature sensor, wherein power for the lighting device and power for the temperature sensor are transmitted on the shared electrical line using a constant current supply with an alternating component or an alternating component portion modulated thereon.

* * * * *